US011857788B2

(12) United States Patent
Manogue

(10) Patent No.: US 11,857,788 B2
(45) Date of Patent: Jan. 2, 2024

(54) METHODS AND APPARATUSES FOR REDUCING BLEEDING VIA COORDINATED TRIGEMINAL AND VAGAL NERVE STIMULATION

(71) Applicant: The Feinstein Institutes for Medical Research, Manhasset, NY (US)

(72) Inventor: Kirk R. Manogue, Sea Cliff, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 55 days.

(21) Appl. No.: 18/150,177

(22) Filed: Jan. 4, 2023

(65) Prior Publication Data

US 2023/0144580 A1    May 11, 2023

Related U.S. Application Data

(63) Continuation of application No. 17/578,339, filed on Jan. 18, 2022, which is a continuation of application No. 16/582,726, filed on Sep. 25, 2019, now Pat. No. 11,260,229.

(60) Provisional application No. 62/736,447, filed on Sep. 25, 2018.

(51) Int. Cl.
*A61N 1/36* (2006.01)
*A61N 1/04* (2006.01)
*A61N 1/05* (2006.01)

(52) U.S. Cl.
CPC ....... *A61N 1/36053* (2013.01); *A61N 1/0456* (2013.01); *A61N 1/0526* (2013.01); *A61N 1/36017* (2013.01); *A61N 1/3606* (2013.01); *A61N 1/36036* (2017.08)

(58) Field of Classification Search
CPC .............. A61N 1/36053; A61N 1/0456; A61N 1/0526; A61N 1/36036; A61N 1/3606; A61N 1/36014
See application file for complete search history.

(56) References Cited

U.S. PATENT DOCUMENTS

| 2,164,121 A | 6/1939 | Pescador |
| 3,363,623 A | 1/1968 | Atwell |
| 3,631,534 A | 12/1971 | Hirota et al. |
| 3,709,228 A | 1/1973 | Barker |

(Continued)

FOREIGN PATENT DOCUMENTS

| CN | 201230913 A | 5/2009 |
| CN | 101528303 A | 9/2009 |

(Continued)

OTHER PUBLICATIONS

US 6,184,239 B1, 02/2001, Puskas (withdrawn)

(Continued)

*Primary Examiner* — Amanda K Hulbert
*Assistant Examiner* — Philip C Edwards
(74) *Attorney, Agent, or Firm* — Shay Glenn LLP

(57) ABSTRACT

Disclosed are apparatuses and methods for reducing or limiting blood loss and reducing bleed time in a subject by combined vagus and trigeminal stimulation. The apparatuses and methods may activate (e.g., electrically) one or more branches of the trigeminal nerve and may concurrently (at overlapping or near-overlapping time) independently activate the vagus nerve. This activation may be invasive or non-invasive.

30 Claims, 6 Drawing Sheets

(56) References Cited

U.S. PATENT DOCUMENTS

| | | |
|---|---|---|
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,514,168 A | 5/1996 | Friedman |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |

(56) References Cited

U.S. PATENT DOCUMENTS

| | | |
|---|---|---|
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,762,032 B1 | 7/2004 | Nelson et al. |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,117,033 B2 | 10/2006 | Shalev et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,010,189 B2 | 8/2011 | Shalev |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,380,315 B2 | 2/2013 | DeGiorgio et al. |
| 8,391,970 B2 | 3/2013 | Tracey et al. |
| 8,412,338 B2 | 4/2013 | Faltys |
| 8,504,161 B1 | 8/2013 | Kornet et al. |
| 8,506,469 B2 | 8/2013 | Dietrich et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,606,371 B2 | 12/2013 | Garfield et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,688,220 B2 | 4/2014 | DeGiorgio et al. |
| 8,696,724 B2 | 4/2014 | Rogers |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,958,880 B2 | 2/2015 | DeGiorgio et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,101,766 B2 | 8/2015 | Nekhendzy |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,579,507 B2 | 2/2017 | Cakmak |
| 9,656,069 B1 | 5/2017 | Danilov et al. |
| 9,656,078 B1 | 5/2017 | Danilov et al. |
| 9,662,490 B2 | 5/2017 | Tracey et al. |
| 9,700,716 B2 | 7/2017 | Faltys et al. |
| 9,789,306 B2 | 10/2017 | Sabourin et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 10,166,395 B2 | 1/2019 | Tracey et al. |

(56) References Cited

U.S. PATENT DOCUMENTS

| | | |
|---|---|---|
| 10,220,203 B2 | 3/2019 | Faltys et al. |
| 10,449,358 B2 | 10/2019 | Levine et al. |
| 10,561,846 B2 | 2/2020 | Tracey et al. |
| 10,583,304 B2 | 3/2020 | Faltys et al. |
| 10,596,367 B2 | 3/2020 | Faltys et al. |
| 10,695,569 B2 | 6/2020 | Levine et al. |
| 10,716,936 B2 | 7/2020 | Faltys et al. |
| 10,912,712 B2 | 2/2021 | Tracey et al. |
| 11,051,744 B2 | 7/2021 | Levine et al. |
| 11,110,287 B2 | 9/2021 | Faltys et al. |
| 11,173,307 B2 | 11/2021 | Levine et al. |
| 11,207,518 B2 | 12/2021 | Huston et al. |
| 11,260,229 B2 | 3/2022 | Manogue |
| 11,278,718 B2 | 3/2022 | Faltys et al. |
| 11,311,725 B2 | 4/2022 | Levine et al. |
| 11,344,724 B2 | 5/2022 | Huston et al. |
| 11,383,091 B2 | 7/2022 | Faltys et al. |
| 11,406,833 B2 | 8/2022 | Faltys et al. |
| 11,471,681 B2 | 10/2022 | Zitnik et al. |
| 11,547,852 B2 | 1/2023 | Levine et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0149145 A1 | 7/2005 | Coulter |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0165459 A1 | 7/2005 | Coulter |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |

(56) References Cited

U.S. PATENT DOCUMENTS

| | | |
|---|---|---|
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234790 A1 | 9/2008 | Bayer et al. |
| 2008/0281197 A1 | 11/2008 | Wiley et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1 | 5/2009 | Shuros et al. |
| 2009/0125079 A1 | 5/2009 | Armstrong et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0312817 A1 | 12/2009 | Hogle et al. |
| 2010/0003656 A1 | 1/2010 | Kilgard et al. |
| 2010/0004709 A1 | 1/2010 | Mische |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0191304 A1 | 7/2010 | Scott |

(56) References Cited

U.S. PATENT DOCUMENTS

| | | |
|---|---|---|
| 2010/0215632 A1 | 8/2010 | Boss et al. |
| 2010/0241183 A1 | 9/2010 | DiLorenzo |
| 2010/0241207 A1 | 9/2010 | Bluger |
| 2010/0249859 A1 | 9/2010 | DiLorenzo |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0145588 A1 | 6/2011 | Stubbs et al. |
| 2011/0152967 A1 | 6/2011 | Simon et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0301658 A1 | 12/2011 | Yoo et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2012/0203301 A1 | 8/2012 | Cameron et al. |
| 2012/0296176 A1 | 11/2012 | Herbst |
| 2013/0013016 A1 | 1/2013 | Diebold |
| 2013/0018439 A1 | 1/2013 | Chow et al. |
| 2013/0066392 A1 | 3/2013 | Simon et al. |
| 2013/0066395 A1 | 3/2013 | Simon et al. |
| 2013/0071390 A1 | 3/2013 | Stadheim et al. |
| 2013/0150756 A1 | 6/2013 | Vitek et al. |
| 2013/0245718 A1 | 9/2013 | Birkholz et al. |
| 2013/0317580 A1 | 11/2013 | Simon et al. |
| 2014/0046407 A1 | 2/2014 | Ben-Ezra et al. |
| 2014/0106430 A1 | 4/2014 | Hargrave et al. |
| 2014/0206945 A1* | 7/2014 | Liao ............ A61B 5/4836 607/45 |
| 2014/0257425 A1 | 9/2014 | Arcot-Krishnamurthy et al. |
| 2014/0277260 A1 | 9/2014 | Khalil et al. |
| 2014/0288551 A1 | 9/2014 | Bharmi et al. |
| 2014/0330335 A1 | 11/2014 | Errico et al. |
| 2014/0343599 A1 | 11/2014 | Smith et al. |
| 2015/0018728 A1 | 1/2015 | Gross et al. |
| 2015/0119956 A1 | 4/2015 | Libbus et al. |
| 2015/0133717 A1 | 5/2015 | Ghiron et al. |
| 2015/0180271 A1 | 6/2015 | Angara et al. |
| 2015/0233904 A1 | 8/2015 | Nayak |
| 2015/0241447 A1 | 8/2015 | Zitnik et al. |
| 2016/0089540 A1 | 3/2016 | Bolea |
| 2016/0158534 A1 | 6/2016 | Guarraia et al. |
| 2016/0250097 A9 | 9/2016 | Tracey et al. |
| 2016/0310315 A1 | 10/2016 | Smith |
| 2016/0331952 A1 | 11/2016 | Faltys et al. |
| 2016/0367808 A9 | 12/2016 | Simon et al. |
| 2017/0007820 A9 | 1/2017 | Simon et al. |
| 2017/0197081 A1 | 7/2017 | Charlesworth et al. |
| 2017/0202467 A1 | 7/2017 | Zitnik et al. |
| 2017/0245379 A1 | 8/2017 | Kang |
| 2017/0304621 A1 | 10/2017 | Malbert et al. |
| 2017/0361093 A1 | 12/2017 | Yoo et al. |
| 2017/0361094 A1 | 12/2017 | Cartledge et al. |
| 2018/0021580 A1 | 1/2018 | Tracey et al. |
| 2018/0085578 A1 | 3/2018 | Rennaker, II et al. |
| 2018/0117320 A1 | 5/2018 | Levine et al. |
| 2018/0289970 A1 | 10/2018 | Faltys et al. |
| 2019/0010535 A1 | 1/2019 | Pujol Onofre et al. |
| 2019/0022389 A1 | 1/2019 | Leonhardt |
| 2019/0192847 A1 | 6/2019 | Faltys et al. |
| 2019/0290902 A1 | 9/2019 | Romero-Ortega et al. |
| 2020/0402656 A1 | 12/2020 | DeBates et al. |
| 2021/0251848 A1 | 8/2021 | Tracey et al. |
| 2021/0315505 A1 | 10/2021 | Levine et al. |
| 2021/0353949 A1 | 11/2021 | Faltys et al. |
| 2022/0040483 A1 | 2/2022 | Levine et al. |
| 2022/0072309 A9 | 3/2022 | Levine et al. |
| 2022/0118257 A1 | 4/2022 | Huston et al. |
| 2022/0193413 A1 | 6/2022 | Levine et al. |
| 2022/0212001 A1 | 7/2022 | Faltys et al. |
| 2022/0212012 A1 | 7/2022 | Manogue |
| 2022/0257941 A1 | 8/2022 | Levine et al. |
| 2022/0280797 A1 | 9/2022 | Faltys et al. |
| 2022/0362555 A1 | 11/2022 | Zitnik et al. |
| 2023/0019961 A1 | 1/2023 | Huston et al. |
| 2023/0117074 A1 | 4/2023 | Zanos et al. |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| EP | 2996764 B1 | 7/2017 |
| EP | 3470111 A1 | 4/2019 |
| GB | 04133 | 2/1910 |
| GB | 2073428 A | 10/1981 |
| JP | 4961558 B2 | 6/2012 |
| JP | 2017035494 A | 2/2017 |
| KR | 20050039445 A | 4/2005 |
| KR | 2016029274 A | 3/2016 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO2016/134197 A1 | 8/2016 |

OTHER PUBLICATIONS

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol .; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al., "On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

(56) References Cited

OTHER PUBLICATIONS

Benoist, et al., "Mast cells in autoimmune disease" Nature., vol. 420(19): pp. 875-878, Dec. 2002.
Benthem et al.; Parasympathetic inhibition of sympathetic neural activity to the pancreas; Am.J.Physiol Endocrinol.Metab; 280(2); pp. E378-E381; Feb. 2001.
Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression In shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioligial aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, Thieme Medical Publishers; pp. 189-204, © 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Caravaca et al.; A novel flexible cuff-like microelectrode for dual purpose, acute and chronic electrical interfacing with the mouse cervical vagus nerve; Journal of Neural Engineering: 14(6);066005; Nov. 1, 2017.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cheyuo et al.; The parasympathetic nervous system in the quest for stroke therapeutics; J. Cereb. Blood Flow Metab.; 31(5); pp. 1187-1195; May 2011.
Cicala et al., "Linkage between inflammation and coagulation: An update on the molecular basis of the crosstalk," Life Sciences, vol. 62(20); pp. 1817-1824. Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroimmunoModulation, vol. 12(5), pp. 307-309, Sep. 2005.
Crusz et al.; Inflammation and cancer; advances and new agents; Nature reviews Clinical Oncology; 12(10); pp. 584-596; doi: 10.1038/nrclinonc.2015.105; Jun. 30, 2015.
Dake; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, Sep. 7, 2000.
De Jonge et al.; Stimulation of the vagus nerve attenuates macrophage activation by activating the Jak2-STAT3 signaling pathway; Nature Immunology; 6(8); pp. 844-851; Aug. 2005.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.

(56) References Cited

OTHER PUBLICATIONS

Ellington et al., In vitro selection of RNA molecules that bind specific ligands, Nature, vol. 346, pp. 818-822, Aug. 30, 1990.
Ellrich et al.; Transcutaneous vagus nerve stimulation; Eur. Neurological Rev.; 6(4); pp. 254-256; Winter 2011.
Emery et al.; Rituximab versus an alternative TNF inhibitor in patients with rheumatoid arthritis who failed to respond to a single previous TNF inhibitor: switch-ra, a global, oberservational, comparative effectiveness study; Annals of the Rheumatic Diseases; 4(6); pp. 979-984; Jun. 2015.
Engineer et al.; Directing neural plasticity to understand and treat tinnitus; Hear. Res.; 295; pp. 58-66; Jan. 2013.
Engineer et al.; Reversing pathological neural activity using targeted plasticity; Nature; 470(7332); pp. 101-104; Feb. 3, 2011 (Author Manuscript).
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF-? ) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gao et al.; Investigation of specificity of auricular acupuncture points in regulation of autonomic function in anesthetized rats; Autonomic Neurosc.; 138(1-2); pp. 50-56; Feb. 29, 2008.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(−)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.
Gottenberg et al.; Non-TNF-targeted biologic vs a second anti-TNF drug to treat rheumatoid arthritis in patients with insufficient response to a first anti TNF drug: a randomized clinical trial; JAMA; 316(11); pp. 1172-1180; Sep. 2016.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; Jul. 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Housley et al.; Biomarkers in multiple sclerosis; Clinical Immunology; 161(1); pp. 51-58; Nov. 2015.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby—Year Book, inc., St. Louis, MO, US, pp. 930-937, Nov. 1, 1999.
Jacob et al.; Detrimental role of granulocyte-colony stimulating factor in neuromyelitis optica: clinical case and histological evidence; Multiple Sclerosis Journal; 18(12); pp. 1801-1803; Dec. 2012.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.
Joshi et al., Potent inhibition of human immunodeficiency virus type 1 replection by template analog reverse transcriptase , J. Virol., 76(13), pp. 6545-6557, Jul. 2002.
Kalishevskaya et al. "The character of vagotomy-and atropin-induced hypercoagulation," Sechenov Physiological Journal of the USSR, 65(3): pp. 398-404, Mar. 1979.

(56) References Cited

OTHER PUBLICATIONS

Kalishevskaya et al.; Nervous regulation of the fluid state of the blood; Usp. Fiziol. Nauk;, vol. 13; No. 2; pp. 93-122; Apr.-Jun. 1982.
Kanai, T. et al., Interleukin-18 and Crohn's disease, Digestion, vol. 63, suppl. 1, pp. 37-42; 2001 (year of pub. sufficiently earlier than effective US filing date and any foreign priority date).
Katagiri, M., et al., Increased cytokine production by gastric mucosa in patients with helicobacter pylori infection, J. Clin, Gastroenterol., vol. 25, Suppl. 1, pp. S211-S214, 1997.
Katsavos et al.; Biomarkers in multiple sclerosis: an up-to-date overview; Multiple Sclerosis International; vol. 2013, Article ID 340508, 20 pages; Jan. 1, 2013.
Kawahara et al.; SIRT6 links histone H3 lysine 9 deacetylation to NF-kappaB-dependent gene expression and organismal life span.; Cell.; vol. 136; No. 1; pp. 62-74; Jan. 2009.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep. 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.
Koopman et al.; Pilot study of stimulation of the cholinergic anti-inflammatory pathway with an implantable vagus nerve stimulation device in patients with rheumatoid arthritis; 2012 ACR/ARHP Annual Meeting, Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only): on Sep. 24, 2020.
Koopman et al.; THU0237 first-in-human study of vagus nerve stimulation for rheumatoid arthritis: clinical and biomarker results through day 84; Annals of the Rheumatic Diseases; 72(Suppl 3):A245; Jun. 1, 2013 (Abstract Only).
Koopman et al.; Vagus nerve stimulation inhibits cytokine production and attenuates disease severity in rheumatoid arthritis; Proceedings of the National Academy of Sciences: 113(29); pp. 8284-8289; Jul. 19, 2016.
Krarup et al; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, Shock, vol. 5, No. 5, pp. 385-388, May 1996.
Kuznik, "Role of the vascular wall in the process of hemostatis," Usp Sovrem Biol., vol. 75(1): pp. 61-85; 1973 (the year of publication is sufficiently earlier than the effective U.S. filing date and any foreign priority date so that the particular month of publication is not in issue).
Kuznik, et al., "Blood Coagulation in stimulation of the vagus nerve in cats," Biull. Eskp. Biol. Med., vol. 78(7): pp. 7-9; 1974 (the year of publication is sufficiently earlier than the effective U.S. filing date and any foreign priority date so that the particular month of publication is not in issue).
Kuznik, et al., "Heart as an efferent regulator of the process of blood coagulation and fibrinolysis," Kardiologiia, vol. 13(3): pp. 10-17; 1973 (the year of publication is sufficiently earlier than the effective U.S. filing date and any foreign priority date so that the particular month of publication is not in issue).
Kuznik, et al., "Role of the heart and vessels in regulating blood coagulation and fibrinolysis," Kagdiologila, vol. 13(4): pp. 145-154, Apr. 1973.
Kuznik, et al., "Secretion of blood coagulation factors into saliva under conditions of hypo-and hypercoagulation," Voprosy Meditsinskoi Khimii, vol. 19(1): pp. 54-57; 1973(the year of publication is sufficiently earlier than the effective U.S. filing date and any foreign priority date so that the particular month of publication is not in issue).
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158; 1975 (the year of publication is sufficiently earlier than the effective U.S. filing date and any foreign priority date so that the particular month of publication is not in issue).
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.
Lipton, J. M et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).
Martindale: The Extra Pharmacopoeia; 28th Ed. London; The Pharmaceutical Press; pp. 446-485; © 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.
McGuinness, P. H., et al., Increases in intrahepatic CD68 positive cells, MAC387 positive cells, and proinflammatory cytokines

(56) References Cited

OTHER PUBLICATIONS (particulary interleukin 18) in chronic hepatitis C infection, Gut, vol. 46(2), pp. 260-269, Feb. 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; Aug. 2004.
Mishchenko, et al., "Coagulation of the blood and fibrinolysos in dogs during vagal stimulation," Sechenov Physiological Journal of the USSR, vol. 61(1): pp. 101-107, 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Molina et al., CNI-1493 attenuates hemodynamic and pro-inflammatory responses to LPS, Shock, vol. 10, No. 5, pp. 329-334, Nov. 1998.
Monaco et al.; Anti-TNF therapy:past,present, and future; International Immunology; 27(1); pp. 55-62; Jan. 2015.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79(2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Olofsson et al.; Single-pulse and unidirectional electrical activation of the cervical vagus nerve reduces tumor necrosis factor in endotoxemia; Bioelectronic Medicine; 2(1); pp. 37-42; Jun. 2015.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Palov et al.; The cholinergic anti-inflammatory pathway: a missing link in neuroimmunomodulation; Molecular Medicine; 9(5); pp. 125-134; May 2003.
Pateyuk, et al., "Treatment of Botkin's disease with heparin," Klin. Med., vol. 51(3): pp. 113-117, Mar. 1973.
Pavlov et al.; The cholinergic anti-inflammatory pathway; Brain, Behavior, and Immunity; 19; p. 493-499; Nov. 2005.
Pavlov et al; Controlling inflammation: the cholinergic anti-inflammatory pathway; Biochem. Soc. Trans.; 34(Pt 6); pp. 1037-1040; Dec. 2006.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Pongratz et al.; The sympathetic nervous response in inflammation; Arthritis Research and Therapy; 16(504): 12 pages; retrieved from the internet (http://arthritis-research.com/content/16/6/504) ; Jan. 2014.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulcerative colitis, N. Engl. J. Med., vol. 330, No. 12, pp. 811-815, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rendas-Baum et al.; Evaluating the efficacy of sequential biologic therapies for rheumatoid arthritis patients with an inadequate response to tumor necrosis factor—alpha inhibitors; Arthritis research and therapy: 13; R25; 15 pages; ; Feb. 2011.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiograma Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Rosas-Ballina et al.; Acetylcholine-synthesizing T cells relay neural signals in a vagus nerve circuit Science; 334(6052); pp. 98-101; 10 pages; (Author Manuscript); Oct. 2011.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukocytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.

(56) References Cited

OTHER PUBLICATIONS

Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); pp. 37R43; Dec. 1986.
Strowig et al.; Inflammasomes in health and disease; Nature; vol. 481; pp. 278-286; doi: 10.1038/nature10759; Jan. 19, 2012.
Sugano et al., Nicotine inhibits the production of inflammatory mediators in U937 cells through modulation of nuclear factor-kappaß activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparison between chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J. et al., Shock and tissue injury induced by recombinant human cachectin, Science, vol. 234, pp. 470-474, Oct. 24, 1986.
Tracey, K. J.; Reflex control of immunity; Nat Rev Immunol; 9(6); pp. 418-428; Jun. 2009.
Tracey, K.J., The inflammatory reflex, Nature, vol. 420, pp. 853-859, Dec. 19-26, 2002.

Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Der Horst et al.; Stressing the role of FoxO proteins in lifespan and disease; Nat Rev Mol Cell Biol.; vol. 8; No. 6; pp. 440-450; Jun. 2007.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.
VanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, Feb. 2000.
Vida et al.; Aplha 7-cholinergic receptor mediates vagal induction of splenic norepinephrine; Journal of Immunology; 186(7); pp. 4340-4346; 16 pages; (Author Manuscript); Apr. 2011.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.
Walland et al., Compensation of muscarinic brochlal effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1.; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.

(56) References Cited

OTHER PUBLICATIONS

Woiciechowsky, C. et al., Sympathetic activation triggers systemic interleukin-10 release in immunodepression induced by brain injury, Nature Med., vol. 4, No. 7, pp. 808-813, Jul. 1998.

Yang et al.; Acetylcholine inhibits LPS-induced MMP-9 production and ccell migration via the alpha7 nAChR-JAK2/STAT3 pathway in RAW264.7 cells; Cellular Physiology and Biochemistry; 36(5); pp. 2025-2038; (the year of publication is sufficiently earlier than the effective U.S. filing date and any foreign priority date so that the particular month of publication is not in issue) 2015.

Yeh, S.S. et al., Geriatric cachexia: the role of cytokines, Am. J. Clin. Nutr., vol. 70(2), pp. 183-197, Aug. 1999.

Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.

Zamotrinsky et al.; Vagal neurostimulation in patients with coronary artery disease; Auton. Neurosci.; 88(1-2); pp. 109-116; Apr. 2001.

Zhang et al., Tumor necrosis factor, The Cytokine Handbook, 3rd ed., Ed. Thompson, Academic Press, pp. 517-548, Jul. 1, 1998.

Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.

Zhang et al.; Roles of SIRT1 in the acute and restorative phases following induction of inflammation.; J Biol Chem.; vol. 285; No. 53; pp. 41391-41401; Dec. 2010.

Zhao et al.; Transcutaneous auricular vagus stimulation protects endotoxemnic rat from lipopolysaccharide-induced inflammation; Evid. Based Complement Alternat. Med.; vol. 2012; Article ID 627023; 10 pages; Dec. 29, 2012.

Zitnik et al.; Treatment of chronic inflammatory diseases with implantable medical devices; Cleveland Clinic Journal of Medicine; 78(Suppl 1); pp. S30-S34; Aug. 2011.

Levine et al.; U.S. Appl. No. 18/151,407 entitled "Control of vagal stimulation," filed Jan. 6, 2023.

* cited by examiner

METHODS AND APPARATUSES FOR REDUCING BLEEDING VIA COORDINATED TRIGEMINAL AND VAGAL NERVE STIMULATION

CROSS REFERENCE TO RELATED APPLICATIONS

This patent application is a continuation of U.S. patent application Ser. No. 17/578,339, filed Jan. 18, 2022, now U.S. patent application Publication No. 2022/0212012, which is a continuation of U.S. patent application Ser. No. 16/582,726, filed Sep. 25, 2019, now U.S. Pat. No. 11,260,229, which claims priority to U.S. Provisional Patent Application No. 62/736,447, filed on Sep. 25, 2018, which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure is generally related to preventing and/or treating bleeding in a subject. More specifically, this disclosure is related to apparatuses (devices, systems, and methods) for preventing and/or treating bleeding and decreasing bleed time in a patient through stimulation of both the trigeminal and vagus nerves, such as through electrical and/or mechanical stimulation of the trigeminal and vagal nerve.

BACKGROUND

Blood is an essential component of an animal's body to transport oxygen, nutrients and waste, protect the body with white blood cells and other immune system functions, and regulate body functions such as pH and hydration within critical ranges. Blood loss may lead to a variety of problems, including dysregulation or ultimately death. Blood loss can occur due to a various causes. For example, there are approximately 100,000,000 surgeries performed annually in the United States, with millions more worldwide (CDC, National Center for Health Statistics) and these generally have an inherent risk of bleeding, from minor to potentially life threatening. Aside from administration of tranexamic acid for select orthopedic procedures, there are no prophylactic systemic therapies available to administer to help improve hemostasis and minimize surgical bleeding.

Trauma is the third leading cause of death in the United States (CDC, National Center for Health Statistics). A common cause of death following traumatic injury is uncontrolled bleeding (CDC, National Center for Health Statistics). While modern tourniquets are sometimes available to help staunch hemorrhage following extremity trauma, these injuries are still dangerous. Approaches to control non-compressible torso hemorrhage remain even more limited and this is a common cause of death of U.S. soldiers on the battlefield.

Postpartum hemorrhage (PPH) is the leading cause of maternal deaths worldwide. The most common cause is poor contraction of the uterus. Other causes include uterine tears, retained placenta, and inadequate blood clotting. In the United States, approximately 11% of maternal deaths result from PPH, whereas in the developing world approximately 60% of maternal deaths result from PPH. This equates to 100,000 to 140,000 deaths per year. Existing treatments include medications such as oxytocin, misoprostol, and ergotamine, intravenous fluids, blood transfusions, and uterine massage. Surgery to repair cervical or vaginal lacerations or uterine rupture is sometimes necessary as well. Many of these therapeutic options are risky or unavailable in resource-poor areas, resulting in dramatically higher mortality rates.

Hemophilia A is an X-linked recessive disorder associated with spontaneous and prolonged bleeding episodes secondary to deficiencies in clotting factor VIII. More than 20,000 individuals in the United States suffer from this life-long disease. Up to 30% of children with severe hemophilia cannot receive standard factor VIII concentrates due to the development of inhibitor antibodies. Maintaining hemostasis then requires bypassing agents, such as activated prothrombin complex concentrate and recombinant factor VIIa, to help generate clot via alternative pathways. These costly therapies are associated with serious systemic thrombotic side effects, including myocardial ischemia, deep venous thrombosis, and pulmonary embolism. Thus there is a need for new devices, methods, and systems to prevent and treat bleeding problems.

Described herein are devices, methods, and systems that may address the issues identified above.

SUMMARY OF THE DISCLOSURE

The present invention relates to controlling bleeding in a patient. More specifically, this disclosure is related to apparatuses (devices, systems) and methods for controlling bleeding and bleed time in a patient through coordinated neural stimulation, such as through electrical and/or mechanical stimulation of both the trigeminal and vagal nerves. The apparatus may provide invasive or, preferably, non-invasive stimulation. The stimulation of the vagus nerve may be overlapping, including concurrent, with the trigeminal never, or the trigeminal nerve and vagus nerve may be alternately (with or without overlap) stimulated. The same amount (one or more of: duration, frequency and/or intensity) of stimulation may be applied to both the vagus nerve and the trigeminal nerve, or the amounts (one or more of: duration, frequency and/or intensity) may be different. In some variations Controlling bleeding may include preventing and/or treating bleeding (e.g., surgical bleeding, traumatic bleeding, bleeding related to other medical procedures or conditions, and inherited or acquired bleeding disorders).

For example, described herein methods of reducing bleed time in a subject that include: applying one or more of mechanical or electrical activation to the subject's trigeminal nerve and the subject's vagus nerve; and reducing bleed time of the bleeding by at least 20%.

Also described herein are methods of reducing bleed time in a subject that has been treated with an anticoagulant, the method comprising: applying one or more of mechanical or electrical activation to the subject's trigeminal nerve; and reducing bleed time of the bleeding by at least 20%.

A method of reducing or limiting blood loss in a hemorrhaging subject may include: applying one or more of mechanical or electrical activation to the subject's trigeminal nerve and the subject's vagus nerve; and reducing blood loss from the hemorrhage by at least 10%.

Also described herein are methods of treating a hemophiliac subject, the method comprising: determining when the subject is bleeding; and applying one or more of mechanical or electrical activation to the subject's trigeminal nerve and the subject's vagus nerve to reduce the blood loss and/or bleeding volume.

In any of these methods, the mechanical and/or electrical stimulation may be applied concurrently (e.g., at the same time), or overlapping in time (partially or completely overlapping) and/or within a few second (e.g., within 1 second, 2 seconds, 3 seconds, 4 seconds, 5 seconds, 6 seconds, 10 seconds, etc.). In some variations the intensity of the vagus nerve stimulation may be less than the stimulation of the trigeminal stimulation (e.g., x% or less, where x is 90%, 85%, 80%, 75%, 70%, 65%, 60%, 55%, 50%, 45%, 40%, 35%, 30%, 25%, 20%, 15%, 10%, or 5% of the trigeminal stimulation). In some variations the intensity of the trigeminal nerve stimulation may be less than the stimulation of the vagus stimulation (e.g., x% or less, where x is 90%, 85%, 80%, 75%, 70%, 65%, 60%, 55%, 50%, 45%, 40%, 35%, 30%, 25%, 20%, 15%, 10%, or 5% of the vagus stimulation). Specifically, the intensity may refer to one or more of the applied voltage or current (e.g., when electrical energy is applied), and/or applied force or pressure (when mechanical stimulation is applied). In some variations the intensity may refer to the duration (e.g., the percentage of the total treatment time that the trigeminal stimulation is active vs. the percentage of the total treatment time that the vagus stimulation is active). In some variations intensity may refer to both the applied energy (voltage, force) and the duration of time energy is applied.

In any of these methods, applying may comprise non-invasively applying one or more of mechanical or electrical activation. Although the methods and apparatuses described herein typically refer to non-invasive application of vagus and/or trigeminal stimulation, alternatively, in any of these methods applying may comprise applying from an implant (e.g., implanted neuromodulator that is in communication with the trigeminal and/or vagus nerve).

In any of these methods, the subject may be human or non-human.

Applying may include applying one or more of mechanical or electrical activation to one or more of an ophthalmic, maxillary and/or mandibular branch of the subject's trigeminal nerve in addition to applying one or more of mechanical or electrical activation to the vagus nerve. For example, applying may comprise applying one or more of mechanical or electrical activation to sensory fibers of the patient's trigeminal nerve. In some variation, applying may be limited to applying via the sensory fibers. In some variations, applying comprises applying unilateral activation to the subject's trigeminal nerve. Alternatively, applying may comprise applying bilateral activation to the subject's trigeminal nerve and/or vagus nerve.

Any of these methods may include reducing bleeding time. For example, reducing bleeding time may comprises reducing bleeding time from of one or more of an internal hemorrhage or an external hemorrhage. Bleeding time may be reduced (e.g., the application of electrical and/or mechanical energy may be applied until the bleeding time is reduced) by more than 10%, 15%, 20%, 25%, 30%, 35%, 40%, 45%, 50%, etc.

Similarly, blood loss may be reduced (e.g., the application of electrical and/or mechanical energy which may be applied until the blood loss is reduced) by more than 10%, 15%, 20%, 25%, 30%, 35%, 40%, 45%, 50%, etc.

Applying may comprise applying electrical stimulation to both the vagus nerve and the trigeminal nerve. For example, applying may comprise applying electrical stimulation at between 1-50 Hz and between 0.5-15 V having a pulse width of between 0.5 ms and 10 ms to the trigeminal nerve and applying electrical stimulation of between 0.5-100 Hz and between 0.2-15 V having a pulse width of between 0.2 ms and 15 ms. Applying may comprise applying for between 1 minute and 45 minutes. Applying may comprise applying electrical stimulation to the trigeminal nerve and mechanical stimulation to the vagus nerve (e.g., in some variations, via the auricular branch).

In any of these methods, applying may comprise applying without triggering a diver's reflex.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 1, the regions (e.g., dermatomes) innervated by the trigeminal nerve are shown one or more of which may be stimulated by the apparatus along with the vagus nerve, shown here schematically applying stimulation to the auricular branch of the vagus nerve.

DETAILED DESCRIPTION

Figure 1:
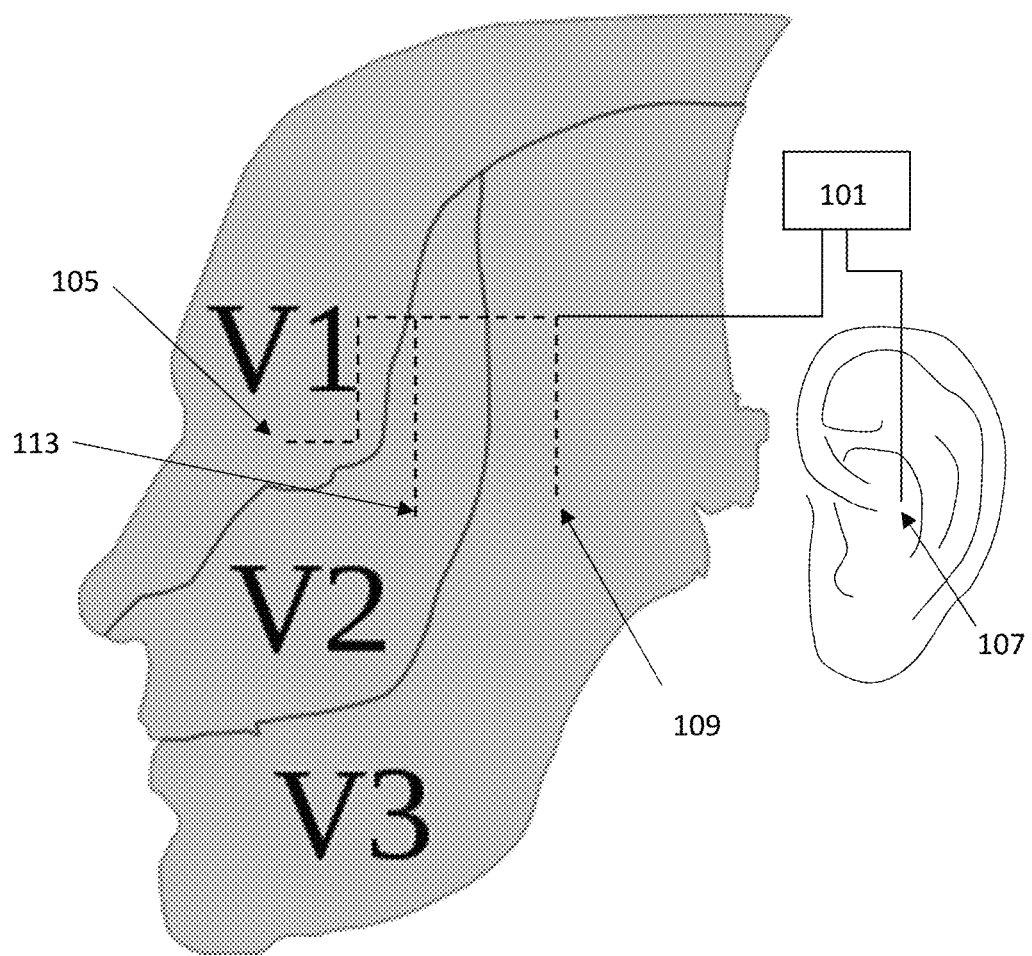
FIG. 1 schematically illustrates a system for stimulation both the trigeminal nerve and the vagus nerve.

The present invention relates to controlling (treating and/or preventing) bleeding in a patient. More specifically, this disclosure is related to apparatuses (devices, systems, and methods) for controlling bleeding and controlling (reducing) bleed time in a patient through neural stimulation, such as through electrical and/or mechanical and/or other stimulation of both (e.g., simultaneously) the trigeminal nerve and the vagus nerve. Controlling bleeding may include preventing and/or treating bleeding (e.g., surgical bleeding, traumatic bleeding, bleeding related to childbirth, bleeding related to other medical procedures or conditions, bleeding mediated or increased by anticoagulants, inherited or acquired bleeding disorders such as hemophilia, and so forth).

"Treatment" as used herein includes prophylactic and therapeutic treatment. "Prophylactic treatment" refers to treatment before onset of a condition (e.g., bleeding, an inflammatory condition, etc.) is present, to prevent, inhibit or reduce its occurrence.

As used herein, a patient or subject may be any animal, preferably a mammal, including a human, but can also be a companion animal (e.g., a cat or dog), a farm animal (e.g., a cow, a goat, a horse, a sheep) or a laboratory animal (e.g., a guinea pig, a mouse, a rat), or any other animal.

"Bleed time" or "bleeding time" as used herein refers to the length of time it takes to for bleeding to stop. In general, it is controlled or influenced by how well blood platelets work to form a platelet plug. Bleed time is generally increased by the administration of anticoagulant, such as aspirin, heparin, and warfarin.

As used herein, the terms "reduce" or "reducing" when referring to bleed time in a subject, encompass at least a small but measurable reduction in bleed time over non-treated controls. Reduction may be at least 5%, at least 10%, at least 20%, at least 30%, at least 40%, at least 50%, at least 60%, or more than 60% or anything in between these ranges. For example, a value between these ranges may be chosen so as to use a protocol or apparatus configured to reduce bleeding while minimizing side effects due to applied trigeminal and vagus nerve stimulation.

The nervous system controls nearly every cell and organ in the body through electrical signals carried by nerves. Such electrical connections allow the nervous system to monitor for tissue injury and then to initiate a healing process. Described herein are apparatuses and methods configured for harnessing such electrical connections via targeted electrical nerve stimulation to effectively treat a variety of conditions. Combined vagus and trigeminal nerve stimulation (VNS/TNS) as described herein is a method to reduce bleeding or bleed time following tissue injury or other bleeding event. Combined vagus and trigeminal nerve stimulation (VNS/TNS) as described herein may be non-invasive or minimally invasive. In some examples, VNS/TNS may be a non-invasive or minimally invasive method to activate the vagus nerve and previously described Neural Tourniquet. The combination of vagus nerve stimulation and trigeminal nerve stimulation may reduce the amount of one or both vagus and trigeminal nerve stimulation necessary for robust reduction of bleed time.

"Combined" vagus and trigeminal nerve stimulation ("VNS/TNS") may refer to the simultaneous (e.g., at the same time), overlapping or near-overlapping (e.g., within about 10 seconds or less, e.g., within 9 sec or less, 8 sec or less, 7 sec or less, 5 sec or less, 2 sec or less, 1 second or less, 0.5 seconds or less, etc.) vagus and trigeminal stimulation.

"Non-invasive stimulation" typically means stimulation that does not require a surgery, exposure of the nerve fiber or direct contact with the nerve fiber. As used herein, "non-invasive stimulation" also does not include administration of pharmacological agents. For example, non-invasive trigeminal nerve stimulation can be achieved, for example, by mechanical (e.g., vibration) or electrical (e.g., electromagnetic radiation) means applied externally to the subject. Similarly non-invasive vagus nerve stimulation may be achieved, for example, by electrical or mechanical (e.g., vibration) stimulation applied externally (e.g., to the auricular region of the ear, over the auricular branch of the vagus nerve.

Although in some examples, a non-invasive or minimally invasive approach as described herein may be used in conjunction with a pharmacological approach (e.g., for an additive or a synergistic benefit), in general an approach described herein may be more efficacious, safer, and less costly than traditional pharmacological therapies. Advantages of this method over pharmacological approaches may include higher specificity, fewer side effects, lower costs, and improved compliance. Advantages over implantable pulse generators for chronic nerve stimulation applications may include avoidance of surgery and associated complications, both for the initial procedure and subsequent procedures for battery changes, and lower costs.

The trigeminal nerve (cranial nerve V) is the largest of the cranial nerves, and has three different branches or nerve distributions (V1, V2, V3; also referred to as the ophthalmic nerve, maxillary nerve and mandibular nerve, respectively) that converge on the trigeminal ganglion. The trigeminal nerve is paired and present on both sides of the body. The trigeminal nerve relays sensory (and motor) information from the head and face. Trigeminal nerve stimulation (TNS) is thought to activate multiple structures in the brain and brainstem, such as the locus coeruleus (LC) and nucleus tractus solitarius (NTS). FIG. 1 shows a schematic of the different skin regions corresponding to the different branches of the trigeminal nerve. The vagus nerve (cranial nerve X) is the longest of the cranial nerves, extending from the brainstem down into the peritoneal cavity. The vagus nerve is the main parasympathetic output of the autonomic nervous system, and interfaces with nearly every organ of the thorax and abdomen, including the heart, lungs, liver, and spleen. Vagus nerve stimulation (VNS) is clinically approved for the treatment of medically refractory epilepsy and depression. Activation of the LC and NTS appears important to the antiepileptic effects of VNS. To date, more than 100,000 patients have received VNS. Technological advances may allow for nerve stimulation without surgical implantation of a pulse generator. For example, transcutaneous auricular stimulation demonstrates anticonvulsive effects similar to invasive VNS.

Direct electrical stimulation of the cervical vagus nerve significantly shortens the duration of bleeding and decreases total blood loss during tissue trauma in swine. Rotational thromboelastography (RoTEG) revealed that VNS significantly shortens the reaction (r) time of blood to initiate clot formation. Moreover, VNS significantly increases thrombin generation at the injury site, whereas systemic thrombin production remains unchanged. Taken together, VNS improves hemostasis by accelerating clot formation specifically at the site of tissue injury.

As described herein VNS/TNS (combined vagus and trigeminal stimulation) may include activating the trigeminal nerve (e.g., by electrical or mechanical or other stimulation) and activating the vagal nerve directly. For example, the vagus nerve may be activated directly in combination with trigeminal nerve activation. Thus a step of controlling bleeding or activating the trigeminal nerve may include a step of directly activating the vagal nerve. Activating the trigeminal nerve may include activating the cholinergic anti-inflammatory pathway and/or any other steps to control bleeding or bleed time in a subject as described in U.S. Pat. No. 8,729,129, while concurrently directly stimulating the vagus nerve. The vagal nerve may be activated either directly or indirectly. In some particular examples, activating the vagus nerve-mediated reduced bleed-time safely and efficaciously may be through stimulation of the trigeminal nerve and the vagus nerve, utilizing precise and specific electrical stimulation parameters. Trigeminal nerve and vagus nerve stimulation may include improving hemostasis via accelerated clot formation such as at the site of tissue injury. This may lead to less blood loss and a shorter duration of bleeding following tissue trauma and hemorrhage.

FIG. 1 shows one example of a schematic for a system configured for the combined stimulation of the vagus and trigeminal nerves. In FIG. 1, the system may include a controller 101 that may include control logic and/or circuitry for driving combined stimulation of the vagus nerve using a vagus nerve stimulation output 107 and a trigeminal nerve stimulation output. In FIG. 1, the trigeminal nerve is shown with three alternatively stimulation outputs 105, 109, 113. One or more branch of the trigeminal nerve may be stimulated by the system; for example, in FIG. 1, the V1 branch of the trigeminal nerve may be mechanically or electrically stimulated by a stimulation output 105 of the system. The V2 branch of the trigeminal nerve may be mechanically or electrically stimulated by a stimulation output 113 of the system. The V3 branch of the trigeminal nerve may be mechanically or electrically stimulated by a stimulation output 109 of the system. For example, one or more electrodes configured to contact the patient's skin over the V1, V2 or V3 branch of the trigeminal nerve may be included. Electrical stimulation may be applied (e.g., pulsed electrical stimulation of between 1-4 kHz at a current of between 0.1 mA to 100 mA). Similarly, the system may include a vagus nerve stimulator 107 that may be connected to the controller 101 to drive stimulation of the vagus nerve. The vagus nerve stimulation may be mechanical stimulator (e.g., configured to apply mechanical force/pressure to the vagus nerve from outside of the body, e.g., by applying against the patient's ear) or an electrical stimulator. For example, the electrical vagus nerve stimulators may apply electrical stimulation from one or more electrodes on the surface of the patient's skin (e.g., the auricular region of the ear). In some variations the electrode may be one or more tissue penetrating electrodes (e.g., needles) inserted into the skin.

In either the vagus or trigeminal stimulators, the apparatus may include a patch (e.g., patch electrode) for contacting part of the body (e.g., head, ear, face, etc.) of a subject and delivering a pulse and a stimulator for providing an electrical stimulus to be delivered through the patch.

Any appropriate electrical or mechanical stimulation may be applied. For example, when applying electrical stimulation to the trigeminal nerve (e.g., through the face), a voltage stimuli (e.g., between 0.2 V to 5 V, at between 0.1-50 Hz, between 0.1 ms and 5 ms pulse width, monophasic and/or biphasic) may be applied for x min (e.g., where x is 2 min, 5 min, 10 minutes, 20 minutes, or 30 minutes, etc.) duration. Vagus nerve stimulation may be applied at approximately or exactly the same time. For example, one complete operational cycle ("dose") may include a 0.2 V-5 V monophasic pulses (e.g., sinusoidal, rectangular, etc. pulses) for a burst duration that is continuous or repeating, with pulses having a duration of between 0.1 ms and 10 ms (e.g., 2 milliseconds). This cycle may be repeated at a repetition rate of between about 0.1 Hz and 1000 Hz (e.g., 30 Hz) for a treatment duration of between 1 min and 40 min (e.g., 10 minutes, 20 minutes, or 30 minutes, etc.). Concurrently stimulation of the vagus nerve may be applied, e.g., through the ear. For example, stimulation of between about 0.1-10 V, 0.1-10 mA, pulsed, e.g., rectangular pulses, for a burst duration that is continuous or repeating, with pulses having a duration of between 0.1 ms and 10 ms (e.g., 2 milliseconds). This cycle may be repeated at a repetition rate of between about 0.1 Hz and 1000 Hz (e.g., 30 Hz) for a treatment duration of between 1 min and 40 min (e.g., 10 minutes, 20 minutes, or 30 minutes, etc.).

Figure 2A:
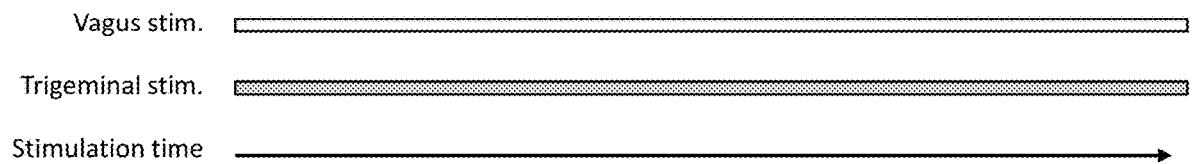
FIGS. 2A-2H illustrate examples of stimulation patterns for simultaneously stimulating both the vagus nerve and the trigeminal nerve.
Figure 2B:
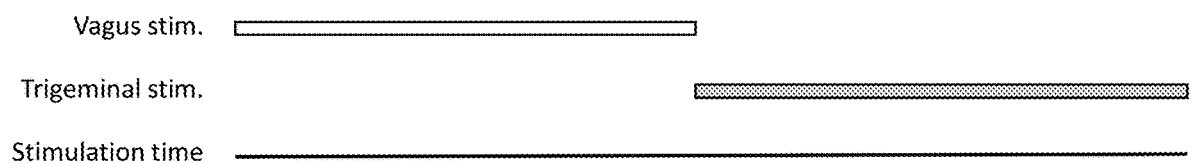

The pattern of concurrent stimulation for the vagus and the trigeminal may be arranged in a variety of different ways. For example, FIGS. 2A-2H illustrate variations of the combined vagus and trigeminal stimulation. In FIG. 2A, the vagus and trigeminal nerve are stimulated at the same time (e.g., same start and stop). This simulation may be identical in frequency (e.g., puling, etc.), and/or intensity (e.g., amplitude, burst duration, etc.). For example, in variations in which both vagus and trigeminal are stimulated electrically by pulsed electrical stimulation, the stimulation may occur at the same time, as shown (e.g., having the same start/stop). Alternatively, in some variations combined vagus nerve and trigeminal nerve stimulation to reduce bleed time may include first stimulating the trigeminal nerve followed by stimulation of the vagus nerve, or by first stimulating the vagus nerve, followed by stimulation of the trigeminal nerve, as shown in FIG. 2A. This alternating stimulation may be repeated for the entire dose duration. In FIG. 2A there is no significant gap between the vagus stimulation and the trigeminal stimulation; in some variations, as shown in FIG. 2D, the combined vagus/trigeminal stimulation includes a gap 217 between the vagus and trigeminal nerve stimulation. As mentioned, this gap may be less than a few second (e.g., 10 seconds or less, 9 seconds or less, 8 seconds or less, 7 seconds or less, 6 seconds or less, 5 seconds or less, 4 seconds or less, 3 seconds or less, 2 seconds or less, 1 seconds or less, 0.5 seconds or less, etc.). The vagus/trigeminal nerve stimulation may therefore alternate and may be repeated for the entire dose duration.

Figure 2C:
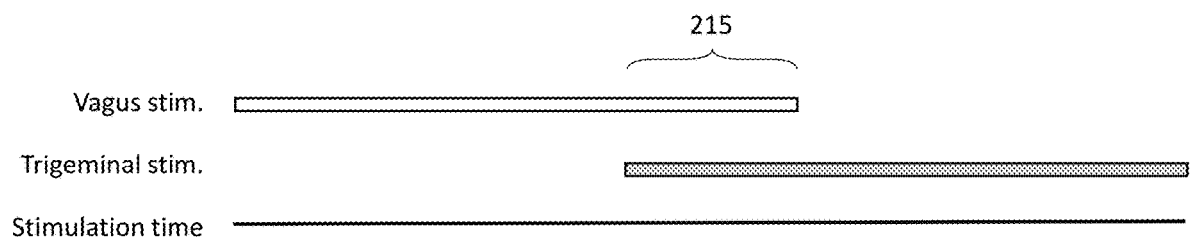
Figure 2D:
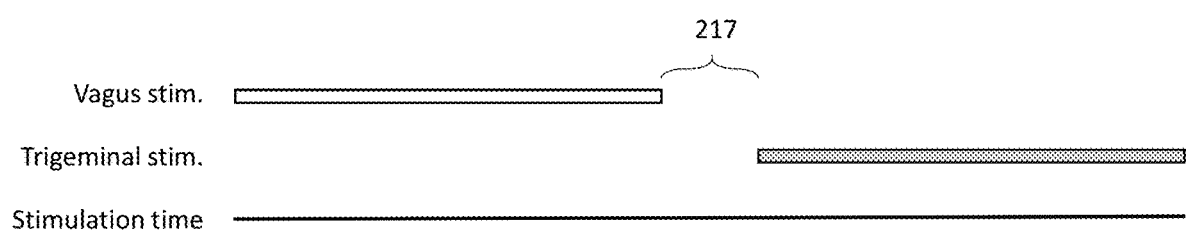

Alternatively, in some variations, as shown in FIG. 2C, the combined vagus and trigeminal stimulation may include overlapping 215 stimulation of the trigeminal and vagus nerve, as shown. In any of these variations, vagus nerve stimulation may begin before trigeminal nerve stimulation (as shown) or in some variations, trigeminal nerve stimulation may begin before vagus nerve stimulation.

Figure 2E:
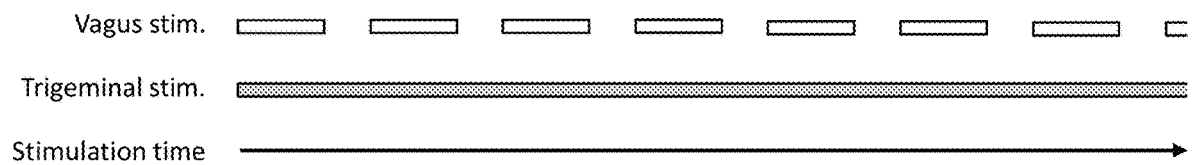

In some variations, either vagus nerve stimulation or trigeminal nerve stimulation may be intermittent and overlap with constant stimulation of the trigeminal (when vagus is intermittent) or vagus (when trigeminal stimulation is intermittent). In FIG. 2E the trigeminal nerve is stimulated continuously (although this may include pulsed or burst of pulses) while the vagus nerve stimulation is intermittent (e.g., turned "on" and "off" with an intermittence frequency) during the dose duration.

Figure 2F:
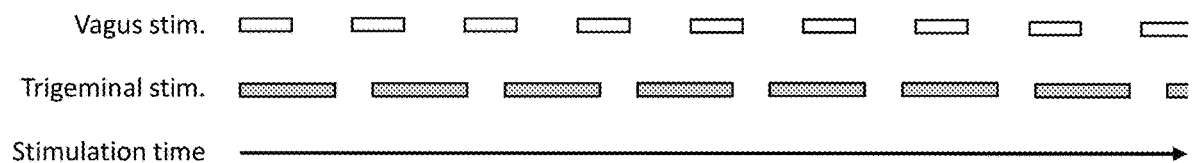
Figure 2G:
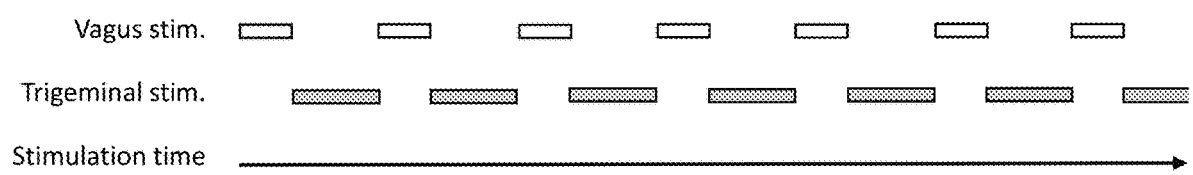
Figure 2H:
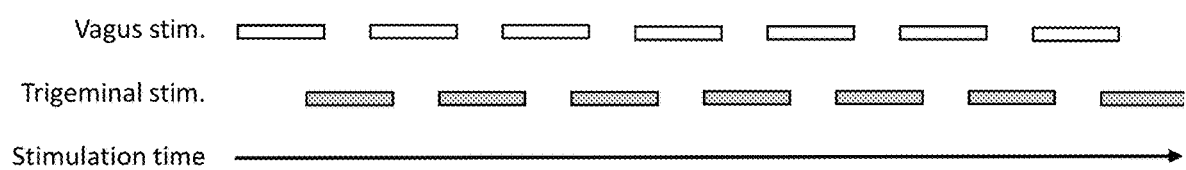

In some variations, as shown in FIG. 2F-2H, combined vagus and trigeminal nerve stimulation to reduce bleeding (e.g., reduce bleed time) may include both vagus nerve stimulation and trigeminal nerve stimulation being pulsed on/off at the same or different frequencies. In FIG. 2F, the vagus nerve stimulation may be performed at an on/off frequency (intermittence frequency) that is different than the trigeminal nerve stimulation frequency; in this example the vagus nerve stimulation has a duty cycle of approximately 50%, while the trigeminal nerve stimulation has a duty cycle of >50% (e.g., >60%, approximately 75%). The vagus nerve stimulation may partially overlap with the trigeminal nerve stimulation during the dose duration, or may not.

In FIG. 2G the combined vagus and trigeminal stimulation to reduce bleeding may include alternating periods of vagus and trigeminal stimulation in which either the vagus nerve stimulation is on for longer than the trigeminal nerve stimulation or the trigeminal nerve stimulation is on for longer than the vagus nerve stimulation (as shown in FIG. 2G). In FIG. 2H, both trigeminal and vagus nerve stimulation are on for the same duration, and the trigeminal and vagus nerve stimulation 'on' times overlap.

In general, the non-invasive stimulation described herein may be non-invasive electrical stimulation applied at a predetermined range of intensities and frequencies. However, other types of non-invasive stimulation may also be used (e.g. non-invasive mechanical stimulation) and can minimally invasive, subcutaneous stimulation. Non-invasive stimulation may be performed by one or more electrodes or actuators that do not contact the nerve. Electrical stimulation may be in the range of 10 mV to 5 V at a frequency of 0.1 Hz to 100 Hz, with a duration of stimulus between from 1 ms to 10 min.

Mechanical stimulation may be oscillatory, repeated, pulsatile, or the like. In some variations the non-invasive stimulation may the repeated application of a mechanical force against the subject's skin at a predetermined frequency for a predetermined period of time. For example, the non-invasive mechanical stimulation may be a mechanical stimulation with a spectral range from 50 to 500 Hz, at an amplitude that ranges between 0.0001-5 mm displacement. The temporal characteristics of the mechanical stimulation may be specific to the targeted disease. In some variations the frequency of stimulation is varying or non-constant. The frequency may be varied between 50 and 500 Hz. In some variations the frequency is constant. In general the frequency refers to the frequency of the pulsatile stimulation within an "on period" of stimulation. Multiple stimulation periods may be separated by an "off period" extending for hours or even days, as mentioned above.

The force with which the mechanical stimulation is applied may also be constant, or it may be variably. Varying the force and/or frequency may be beneficial to ensure that the mechanical stimulation is effective during the entire period of stimulation, particularly if the effect of non-invasive stimulation operates at least in part through mechanoreceptors such as the rapidly acclimating Pacinian corpuscles.

In performing any of the therapies described herein, the non-invasive stimulation may be scheduled or timed in a specific manner. For example, a period of stimulation ("on stimulation") may be followed by a period during which stimulation is not applied ("off period"). The off period may be much longer than the on period. For example, the off period may be greater than an hour, greater than two hours, greater than four hours, greater than 8 hours, greater than 12 hours, greater than 24 hours, or greater than 2 days. The on period is the duration of a stimulation (which may include a frequency component), and may be less than 10 minutes, less than 5 minutes, less than 2 minutes, less than 1 minute, etc. The ratio of the on period and the off period may partially determine the duty cycle of stimulation.

In some examples, either one (e.g., left or right) of the two paired trigeminal nerves may be activated (e.g., unilateral activation). In some examples, the paired trigeminal nerves may be both be activated in a subject (e.g., bilateral activation). In some examples, part or all of the trigeminal nerve may be activated. For example, any one, two or three of the three different branches or nerve distributions (V1, V2, V3; also referred to as the ophthalmic nerve, maxillary nerve and mandibular nerve, respectively) may be activated. In some examples, sensory fibers of the trigeminal nerve are stimulated. Additionally, the trigeminal ganglion may also or instead be stimulated. Additionally or instead, associated neurons that are connected to the trigeminal nerve may be stimulated.

Stimulation may be performed using one or more patches configured to cover part of the body each containing one or more electrodes (an array of 2, 3, 4, 5, 10, or more electrodes) configured to cover part of the body (e.g. cheek, forehead, head, neck, nose, scalp, etc.) in a position sufficient to provide stimulation one or more parts of a trigeminal nerve. Stimulation may be performed using one or more electrodes configured to be placed under the skin, such as in a muscle and 1, 2, 3, 4, 5, 10, or more electrodes) may be placed in a muscle.

Also described herein are apparatuses (devices, systems, and methods) for activating the trigeminal nerve and the vagal nerve. In some embodiments, both the trigeminal nerve and the vagal nerve may be directly activated (e.g., by electrical, mechanical or other stimulation such as magnetic, thermal, etc.).

Further, in some variations, the trigeminal stimulation described herein may not activate the dive reflex. The dive reflex in general can activated, for example, by submerging the body in cold water (and holding the breath) wherein the body overrides basic homeostatic functions. The dive reflex is a physiological adaptation that regulates respiration, heart rate, and arterial blood pressure in a particular way. Although all mammals control breathing, heart rate, and arterial blood pressure during their lives, these controls are strongly altered during diving and activation of the dive reflex. In general, trigeminal stimulation parameters may be chosen so as to not activate the dive reflex (e.g., trigeminal stimulation without inducing a dive reflex). Failure to induce a dive reflex may be failure to invoke a percentage change in heart rate and/or respiration and/or arterial blood pressure by more than a predetermined amount. For example, failure to induce a dive reflex may be failure to reduce one or more of heart rate and/or respiration and/or arterial blood pressure by greater than about 2%, 5%, 7%, 10%, 15%, 20%, 25%, 30%, 40%, etc.

The apparatuses and methods described herein may be suitable for therapeutically or prophylactically treating subjects suffering from or at risk from suffering from unwanted bleeding from any cause such as: bleeding disorders including but not limited to afibrinogenemia, Factor II deficiency, Factor VII deficiency, fibrin stabilizing factor deficiency, Hageman Factor deficiency, hemophilia A, hemophilia B, hereditary platelet function disorders (e.g., Alport syndrome, Bernard-Soulier Syndrome, Glanzmann thrombasthenia, gray platelet syndrome, May-Hegglin anomaly, Scott syndrome, and Wiskott-Aldrich syndrome), parahemophilia, Stuart Power Factor deficiency, von Willebrand disease, thrombophilia, or acquired platelet disorders (such as those caused by common drugs: antibiotics, and anesthetics, blood thinners, and those caused by medical conditions such as: chronic kidney disease, heart bypass surgery, and leukemia), childbirth, injury, menstruation, and surgery. An unwanted bleeding treated using any of the apparatuses or methods described herein may include an internal hemorrhage or an external hemorrhage. An internal hemorrhage includes a hemorrhage in which blood is lost from the vascular system inside the body, such as into a body cavity or space. An external hemorrhage includes blood loss outside the body.

EXAMPLES

Figure 3A:
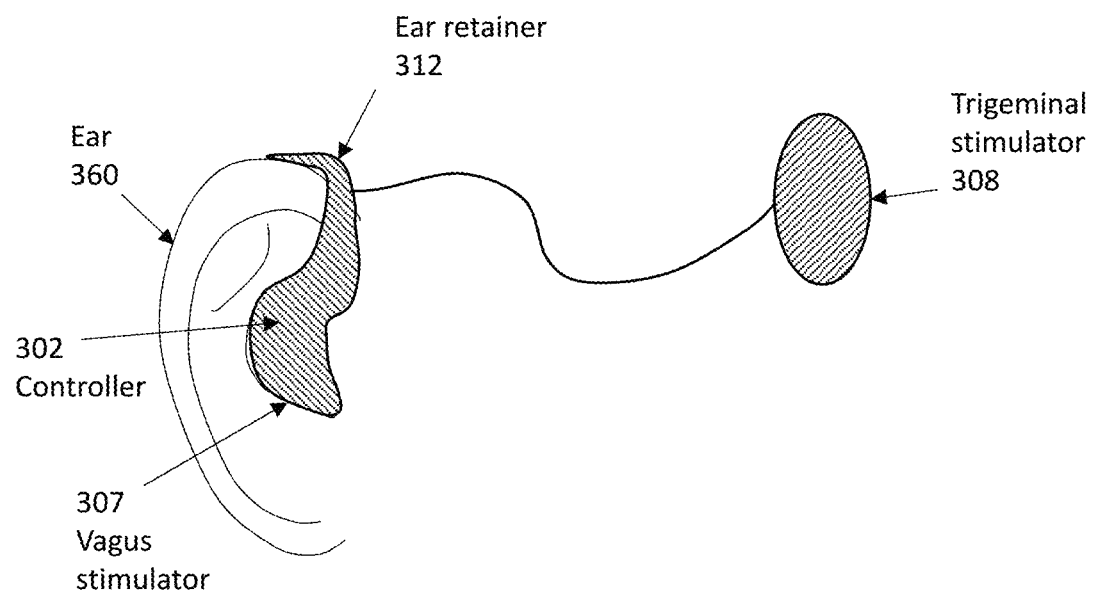
FIGS. 3A-3D illustrate examples of systems that may be used to simultaneously stimulate both the vagus nerve and the trigeminal nerve to reduce bleed time.

FIG. 3A illustrates one example of a combined trigeminal and vagus nerve stimulator for treating bleeding (e.g., for reducing bleed time) as described. In FIG. 3A, the apparatus includes a housing that is configured or adapted to fit over, behind and at least partially into the patient's auricle region of the ear. The housing may include an ear retainer 312 for holding the device in/on the ear 360, and may at least partially enclose a controller (e.g., control circuitry, a battery, power control circuitry, waveform generator, a trigeminal stimulation drive and vagus stimulation drive). The apparatus also includes a vagus stimulator 307 that is coupled to the housing in this example, to be applied against the patient's ear. A connector (e.g., cable, wire, etc.) connects a trigeminal stimulator 308 that may be worn on the patient's face (e.g., in the V1, V2 and/or V3 region, as shown in FIG. 1). The controller may be connected (via a wire or wireless connection) to a user interface that may control starting/stopping of the dose, or in some variations the housing may include a control (e.g., button, dial, etc.). The dose may be preprogrammed into the controller and/or it may be adjusted.

Figure 3B:
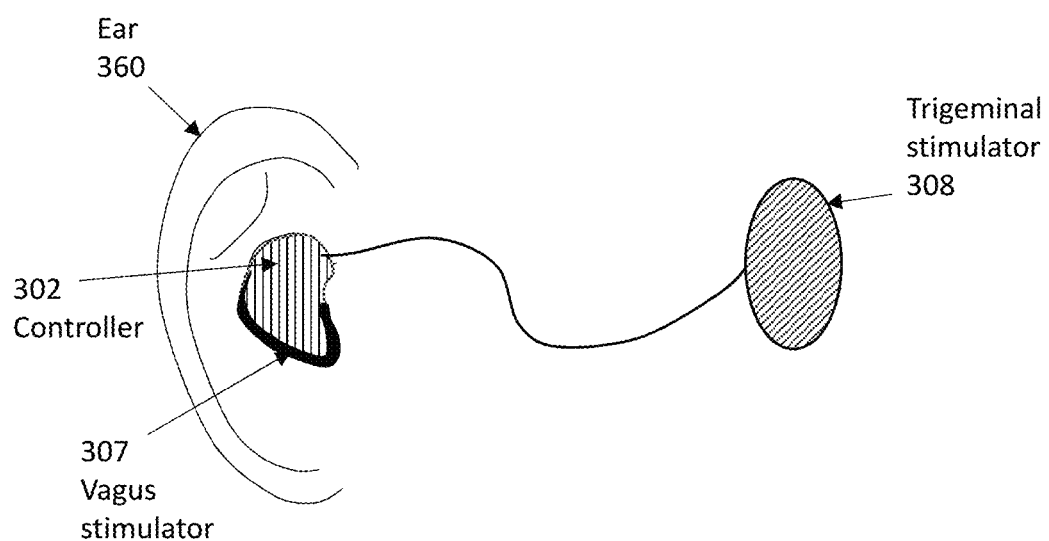

FIG. 3B shows another example of a combined trigeminal and vagus nerve stimulator for treating bleeding (e.g., for reducing bleed time) as described. In FIG. 3B, the apparatus includes a housing that is configured or adapted to fit at least partially into the patient's ear, as shown. The housing may be held in the ear 360, and may include a foam or other expandable material to help secure it in place. Alternatively a separate retainer may be used to hold it in/on the ear (not shown). The housing may at least partially enclose a controller (e.g., control circuitry, a battery, power control circuitry, waveform generator, a trigeminal stimulation drive and vagus stimulation drive). The apparatus may also include a vagus stimulator 307 that is coupled to the housing in this example, to be applied against the patient's ear. A connector (e.g., cable, wire, etc.) connects a trigeminal stimulator 308 that may be worn on the patient's face (e.g., in the V1, V2 and/or V3 region, as shown in FIG. 1). The controller may be connected (via a wire or wireless connection) to a user interface that may control starting/stopping of the dose, or in some variations the housing may include a control (e.g., button, dial, etc.). The dose may be preprogrammed into the controller and/or it may be adjusted.

Figure 3C:
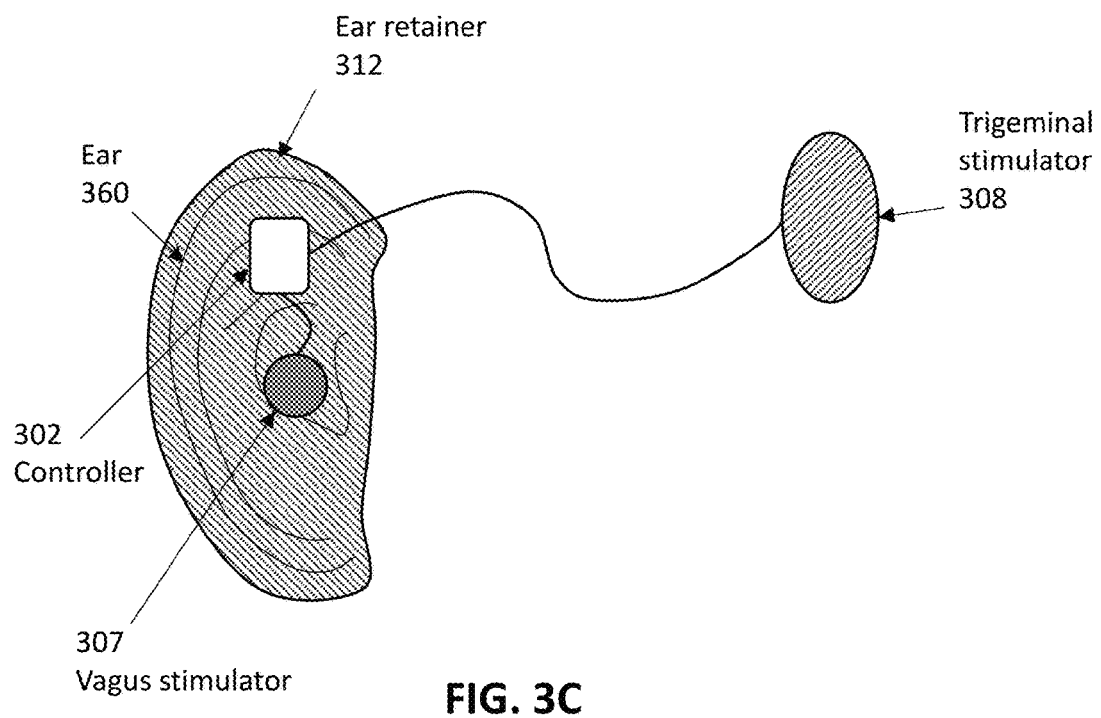

FIG. 3C is another example of a combined trigeminal and vagus nerve stimulator for treating bleeding (e.g., for reducing bleed time) as described. In FIG. 3C, the apparatus include an ear retainer 312 that is configured or adapted to fit at least partially over the patient's ear, as shown. The retainer holds the device over the patient's ear 360, so that the vagus stimulator 307 is in contact with the region of the ear over the vagus nerve. The retainer also holds the controller 302 and may be formed of a material (e.g., mesh, etc.) that fits over the ear to help secure it in place. The controller (e.g., control circuitry, a battery, power control circuitry, waveform generator, a trigeminal stimulation drive and vagus stimulation drive) may be held by the retainer; the vagus nerve stimulator may include a biocompatible adhesive (e.g., hydrogel, etc.) for making electrical contact with the ear. A connector (e.g., cable, wire, etc.) connects the controller with a trigeminal stimulator 308 that may be worn on the patient's face (e.g., in the V1, V2 and/or V3 region, as shown in FIG. 1). The controller may be connected (via a wire or wireless connection) to a user interface that may control starting/stopping of the dose, or in some variations the housing may include a control (e.g., button, dial, etc.). The dose may be preprogrammed into the controller and/or it may be adjusted.

Figure 3D:
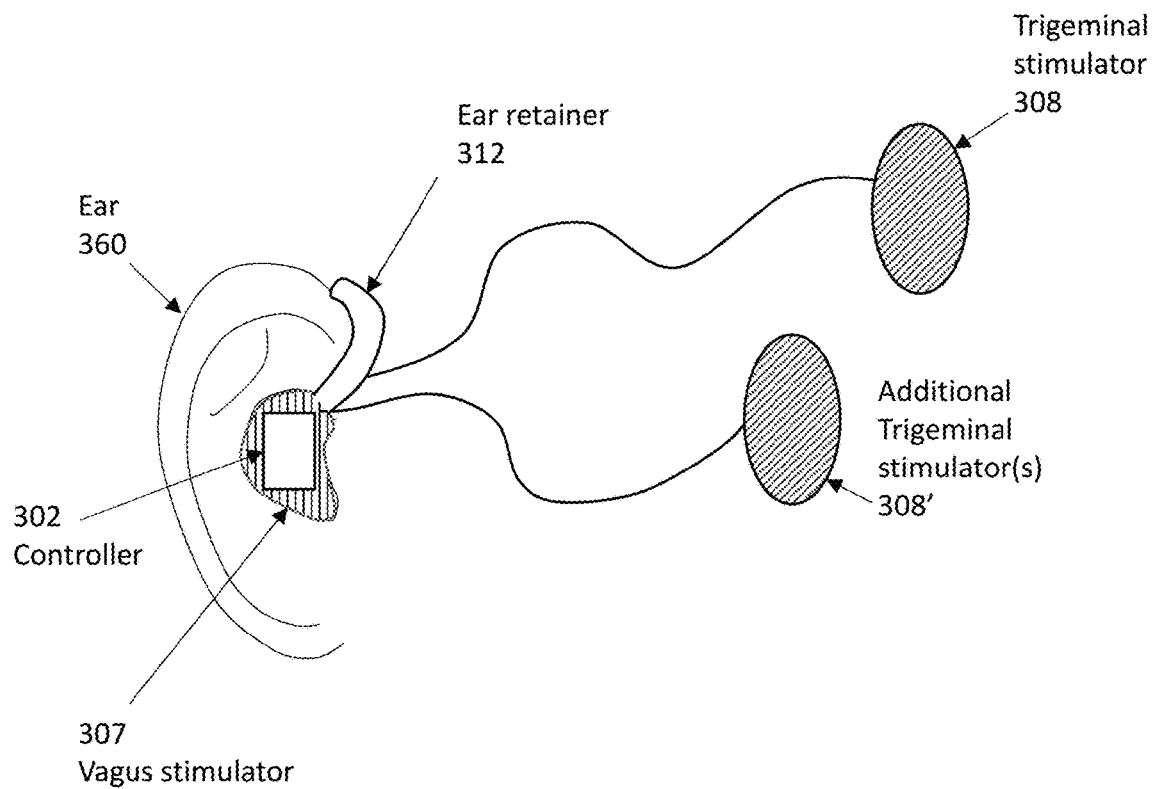

FIG. 3D is another example of a combined trigeminal and vagus nerve stimulator for treating bleeding (e.g., for reducing bleed time) as described. In FIG. 3D, the apparatus is configured or adapted to fit at least partially into the patient's ear, as shown. The apparatus may be held in the ear 360 by an ear retainer 312 to secure it in place. The retainer may fit over the back of the ear and/or partially under the ear to hold the apparatus in/on the ear. In FIG. 3D, the controller (e.g., control circuitry, a battery, power control circuitry, waveform generator, a trigeminal stimulation drive and vagus stimulation drive) is shown on the front; in some variations the controller may be on the back of the apparatus (e.g., held behind the ear). The apparatus may also include a vagus stimulator 307 that is configured to contact the ear. A connector (e.g., cable, wire, etc.) connects the controller to a first trigeminal stimulator 308 that may be worn on the patient's face (e.g., in the V1, V2 and/or V3 region, as shown in FIG. 1). One or more additional trigeminal stimulators 308' may be connected as well (e.g., in parallel or in series with the first trigeminal stimulator). Thus, multiple sites may be used for trigeminal stimulation. The controller may be connected (via a wire or wireless connection) to a user interface that may control starting/stopping of the dose, or in some variations the housing may include a control (e.g., button, dial, etc.). The dose may be preprogrammed into the controller and/or it may be adjusted.

In any of these apparatuses, the vagus stimulator (vagus nerve stimulator) may be an electrical or a mechanical stimulator. In variations in which the apparatus is an electrical stimulator, the vagus stimulator may include one or more electrodes that may be coupled to the patient's skin and/or may penetrate into the skin (e.g., as shallow needle electrodes). The electrodes may apply electrical energy to modulate the vagus nerve, as descried herein. Mechanical stimulators may apply mechanical energy as described above. Similarly, any of these apparatuses may include one or more trigeminal stimulators that may be configured to apply electrical stimulation (e.g., including one or more electrodes, which may include a hydrogel for making skin contact). The trigeminal stimulators may alternatively be mechanical stimulators.

In any of the methods and apparatuses described herein, VNS/TNS can modulate both the patient's sympathetic nervous system (SNS) and parasympathetic nervous system (PNS) activities to reduce bleed time.

As mentioned above, any of these methods and apparatuses may be configured to non-invasively applying neuromodulation of the trigeminal nerve and vagus nerve. Alternatively or additionally, invasive (e.g., using a needle electrode, implant, etc.) may be used for either VNS, TNS or both VNS and TNS.

For example, non-invasive trigeminal stimulation may be applied via one or more skin surface electrodes that apply trigeminal stimulation to one or more of the subject's forehead, cheek(s), nose, tongue, or other facial skin. In some embodiments, applying the non-invasive neurostimulation to the subject's trigeminal nerve includes targeting at least one of the ophthalmic nerve, maxillary nerve, or mandibular nerve. Alternatively, in some variations, applying non-invasive neurostimulation to the subject's trigeminal nerve includes avoiding targeting at least one of the ophthalmic nerve, maxillary nerve, or mandibular nerve.

Any appropriate frequency and/or amplitude and/or duration may be used. In some embodiments, applying the non-invasive neurostimulation to the subject's trigeminal nerve comprises non-invasive neurostimulation has a frequency of 1-300 (e.g., between 10-60 Hz, etc.). In some embodiments, the non-invasive neurostimulation has an intensity of 2 mV-20 V (e.g., between 0.5 V and 15 V, between 1 V and 12 V, etc.). In some embodiments, the non-invasive neurostimulation has a duty cycle of between about 20% to 70% (e.g., 1 second "on" and 1-2 seconds "off"). In some embodiments, the non-invasive neurostimulation includes a pulse width of between about 0.1 ms to 10 ms (e.g., between about .1 ms to 5 ms, between about 0.25 to 5 ms, etc.). In some embodiments, at least one of a stimulation voltage or a current is increased gradually (e.g., steps of 0.1 V). In some embodiments, the closed-loop trigeminal and/or vagus nerve stimulation is conducted based on a heart rate of the patient (e.g., subject). In some embodiments, the closed-loop trigeminal nerve stimulation is conducted based on a heart rate variability (HRV) of the patient. In some embodiments, certain parameters of the stimulation are modulated to maintain values of the parameters within a target range (e.g., preventing a hear rate or blood pressure effect, etc.).

Figure 4:
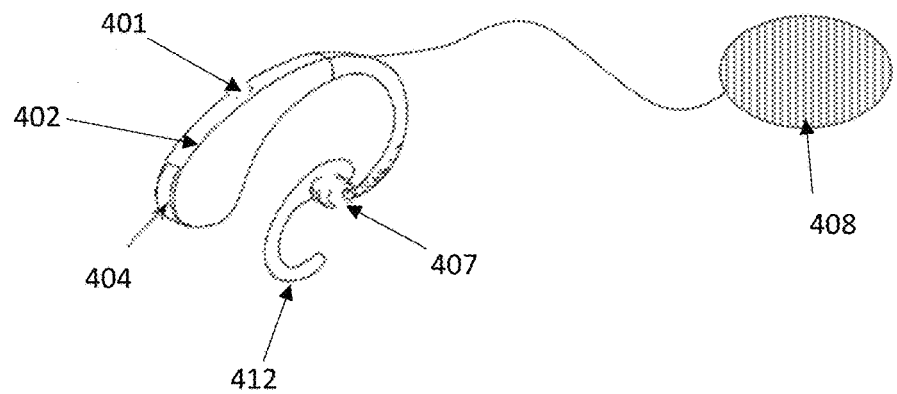
FIG. 4 is an example of a device for reducing bleed time by simultaneously stimulating both the vagus nerve and the trigeminal nerve.

FIG. 4 is another example of a combined vagus and trigeminal nerve stimulator for reducing bleeding (e.g., reducing bleed time). In FIG. 4, the apparatus includes a housing 401 enclosing a controller 402 (e.g., control circuitry) and a battery 404. The housing is configured to fit behind a patient's ear (not shown), and insert a vagus stimulator 407 into the ear so that it is in contact with the region above the auricular branch of the vagus nerve. In FIG. 4 the apparatus also includes an additional retainer 412 to help anchor the vagus stimulator. A trigeminal stimulator 408 is connected to the controller as well (the connection shown in a wire). The trigeminal stimulator may be an electrode pad that is in electrical communication with the controller (e.g., driver, waveform generator, etc.); similarly the vagus stimulator may include an electrode (or electrode pad) that is in electrical communication with the controller.

Figure 5:
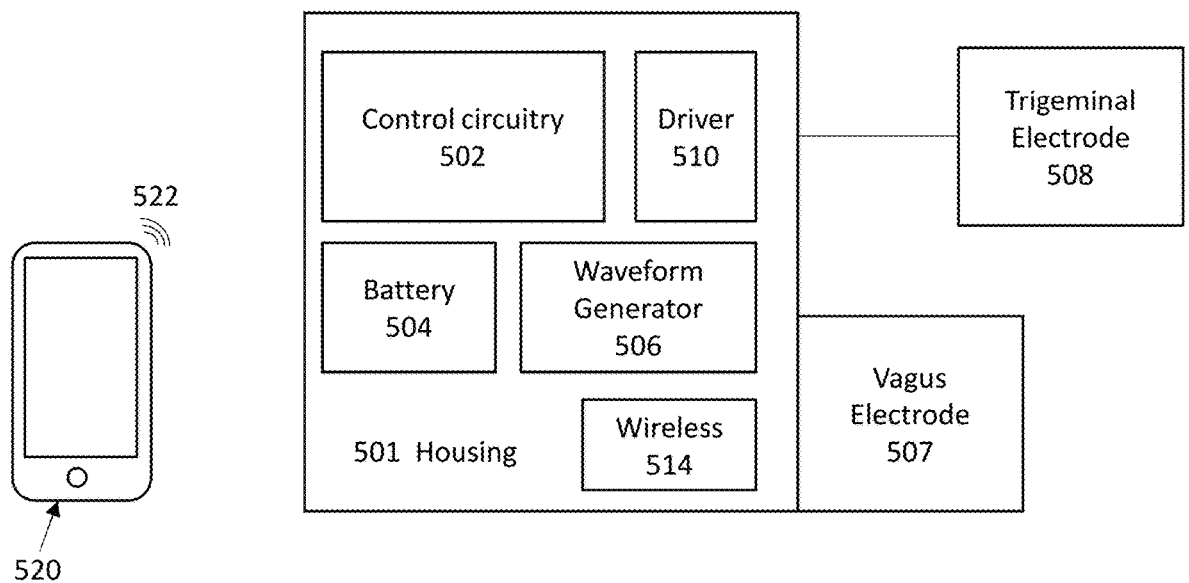
FIG. 5 schematically illustrates a system for reducing bleed time by simultaneously stimulating both the vagus nerve and the trigeminal nerve.

FIG. 5 schematically illustrates some of the components of an apparatus for combined vagus and trigeminal stimulation to reduce bleeding as described above in FIGS. 3A-4. In the schematic of FIG. 5, the controller 502 may be separate from or integrated with one or more drivers 510 and waveform generators 506 that may generate and provide power to the trigeminal stimulator (e.g., shown here as a trigeminal electrode 508) and vagus stimulator (shown as a vagus electrode 507). The controller may also be connected to or include wireless communication circuitry 514 for wirelessly communicating 522 with one or more external devices 520 (shown in this example as a smartphone, though any external processor may be used). In FIG. 5, the controller (including control circuitry) may be housed within a housing 501. In some variations this housing may be configured or adapted to fit into, on and/or over a patient's ear (generically referred to as on the patient's ear).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for accelerating clot formation at an injury site of a patient using non-invasive electrical stimulation, the system comprising:
    an apparatus configured to be worn upon a portion of a head and/or neck of a patient, wherein
        the apparatus comprises at least two electrodes,
        a first electrode of the at least two electrodes configured to be disposed in a region of a branch of the trigeminal nerve, and
        a second electrode of the at least two electrodes configured to be disposed in a region of a branch of the vagus nerve; and
    a controller in electrical communication with the at least two electrodes, the controller being configured to deliver, via the apparatus, electrical stimulation for accelerating clot formation, wherein
        the electrical stimulation comprises, over a time period of at least five minutes,
        applying electrical trigeminal nerve stimulation (TNS) pulses to the trigeminal nerve via the first electrode, and
        simultaneous with, overlapping with, and/or near-overlapping with application of the electrical TNS pulses, applying electrical vagal nerve stimulation (VNS) pulses to the vagus nerve via the second electrode, and
        the electrical stimulation is configured to significantly accelerate clot formation at an injury site of the patient.

2. The system of claim 1, wherein the electrical stimulation is repeated approximately every 24 hours.

3. The system of claim 1, wherein the branch of the trigeminal nerve is a maxillary branch.

4. The system of claim 1, wherein the branch of the vagus nerve is an auricular branch.

5. The system of claim 1, wherein the controller comprises wireless communication circuitry for wirelessly communicating with one or more external devices.

6. The system of claim 1, wherein the apparatus comprises a housing configured for positioning such that portions of the housing contact skin of an ear of the patient and/or skin proximate to the ear, wherein the at least two electrodes are mounted to one or more surfaces of the housing.

7. The system of claim 1, wherein the apparatus comprises a connector for electrically connecting the apparatus to the controller.

8. The system of claim 1, wherein the electrical stimulation is delivered prophylactically to the patient due to risk of future bleeding.

9. The system of claim 8, wherein the electrical stimulation is applied prior to a medical procedure.

10. The system of claim 9, wherein the medical procedure is a surgical procedure.

11. The system of claim 8, wherein the risk of future bleeding is due at least in part to a bleeding disorder of the patient.

12. The system of claim 11, wherein the bleeding disorder is hemophilia or Von Willebrand Disease.

13. The system of claim 1, wherein accelerating clot formation comprises increasing thrombin generation at the injury site of the patient in comparison to thrombin generation in a non-treated patient, while systemic thrombin generation remains unchanged.

14. The system of claim 1, wherein the electrical stimulation is configured to modulate parasympathetic nervous system (PNS) activities.

15. The system of claim 1, wherein the controller comprises a user interface configured to enable a user to adjust the electrical stimulation.

16. The system of claim 1, wherein:
    applying the electrical VNS stimulation comprises applying the electrical TNS stimulation at a first frequency between 31 and 150 Hz; and
    applying the electrical TNS stimulation comprises applying the electrical VNS stimulation at a second frequency between 1 and 30 Hz.

17. The system of claim 1, wherein the electrical stimulation is configured to reduce a bleed time and/or bleed volume of a current or future bleeding event of the patient by at least 10%.

18. The system of claim 17, wherein the risk of future bleeding is due to menstruation in the patient.

19. The system of claim 1, wherein the first electrode and the second electrode are in non-penetrating contact with skin of the patient.

20. A method for accelerating clot formation, comprising:
providing an apparatus to be worn upon a portion of a head and/or neck of a patient, the apparatus comprising at least two electrodes, wherein, when the apparatus is worn by the patient,
a first electrode of the at least two electrodes is disposed in a region of a branch of the trigeminal nerve, and
a second electrode of the at least two electrodes is disposed in a region of a branch of the vagus nerve; and
delivering, via a controller in electrical communication with the at least two electrodes, electrical stimulation for accelerating clot formation, wherein
the electrical stimulation comprises, over a time period of at least five minutes, applying electrical trigeminal nerve stimulation (TNS) pulses to the trigeminal nerve via the first electrode, and
simultaneous with, overlapping with, and/or near-overlapping with application of the electrical TNS pulses, applying electrical vagal nerve stimulation (VNS) pulses to the vagus nerve via the second electrode, and
the electrical stimulation is configured to significantly accelerate clot formation at a current or future injury site of the patient.

21. The method of claim 20, wherein the electrical stimulation is configured to significantly increase thrombin generation at an injury site of the patient in comparison to thrombin generation in a non-treated patient, while systemic thrombin generation remains unchanged.

22. The method of claim 20, wherein the at least two electrodes are non-penetrating electrodes.

23. The method of claim 20, wherein the VNS pulses are applied such that the cervical branch of the vagus nerve is stimulated.

24. The method of claim 20, wherein the at least two electrodes are configured to penetrate tissue.

25. The method of claim 20, wherein the VNS pulses are applied such that an auricular branch of the vagus nerve is stimulated.

26. The method of claim 20, wherein the TNS pulses are applied such that an auriculotemporal branch of the trigeminal nerve is stimulated.

27. The method of claim 20, wherein the electrical stimulation is delivered prophylactically to the patient due to risk of future bleeding.

28. The method of claim 27, wherein the risk of future bleeding is due at least in part to a bleeding disorder of the patient.

29. The method of claim 28, wherein the bleeding disorder is hemophilia or Von Willebrand Disease.

30. The method of claim 20, wherein the electrical stimulation is configured to reduce a bleed time and/or bleed volume of a current or future bleeding event of the patient by at least 10%.

* * * * *